United States Patent
Witteveen et al.

(10) Patent No.: US 6,746,529 B1
(45) Date of Patent: Jun. 8, 2004

(54) STABLE, SPRAY-DRIED COMPOSITION IN A CARBOHYDRATE SUBSTRATE AND PROCESS FOR OBTAINING SAID COMPOSITION

(75) Inventors: Frans Witteveen, Leusden (NL); Roelof Orsel, Huizen (NL); Jack Burger, Almere (NL); Louis Doorn, Zeewolde (NL)

(73) Assignee: Quest International, B.V., Naarden (NL)

( * ) Notice: Subject to any disclaimer, the term of this patent is extended or adjusted under 35 U.S.C. 154(b) by 74 days.

(21) Appl. No.: 10/130,364
(22) PCT Filed: Nov. 17, 2000
(86) PCT No.: PCT/NL00/00840
§ 371 (c)(1), (2), (4) Date: May 17, 2002
(87) PCT Pub. No.: WO01/35764
PCT Pub. Date: May 25, 2001

(30) Foreign Application Priority Data

Nov. 18, 1999 (EP) .............................................. 99203854
Nov. 26, 1999 (EP) .............................................. 99203981

(51) Int. Cl.[7] .......................... C08L 5/02; C09D 105/02
(52) U.S. Cl. .................................. 106/205.71; 424/439
(58) Field of Search ....................... 106/205.71, 207.71; 424/439

(56) References Cited

U.S. PATENT DOCUMENTS

| 4,532,145 A | * | 7/1985 | Saleeb et al. ................ 426/650 |
| 5,087,461 A | * | 2/1992 | Levine et al. ................. 426/96 |
| 5,124,162 A | * | 6/1992 | Boskovic et al. ............. 426/96 |

FOREIGN PATENT DOCUMENTS

| EP | 0 426 428 A1 | 5/1991 |
| EP | 0 545 632 A1 | 6/1993 |

* cited by examiner

Primary Examiner—Helene Klemanski
(74) Attorney, Agent, or Firm—Fitch, Even, Tabin & Flannery

(57) ABSTRACT

The invention relates to a moisture and oxygen stable spray-dried composition comprising at least one active compound encapsulated in a carbohydrate matrix, which matrix is characterized by
- 40 to 80 wt. % high molecular weight film forming carbohydrate;
- 10 to 30 wt. % mono, di and trisaccharides; and
- 10 to 30 wt. % maltodextrin, based on the total weight of the carbohydrate matrix. The active compound to be encapsulated in the carbohydrate matrix can be selected from the group consisting of flavourants, fragrances, pharmaceuticals and wash-active components.

25 Claims, 3 Drawing Sheets

Figure 1:
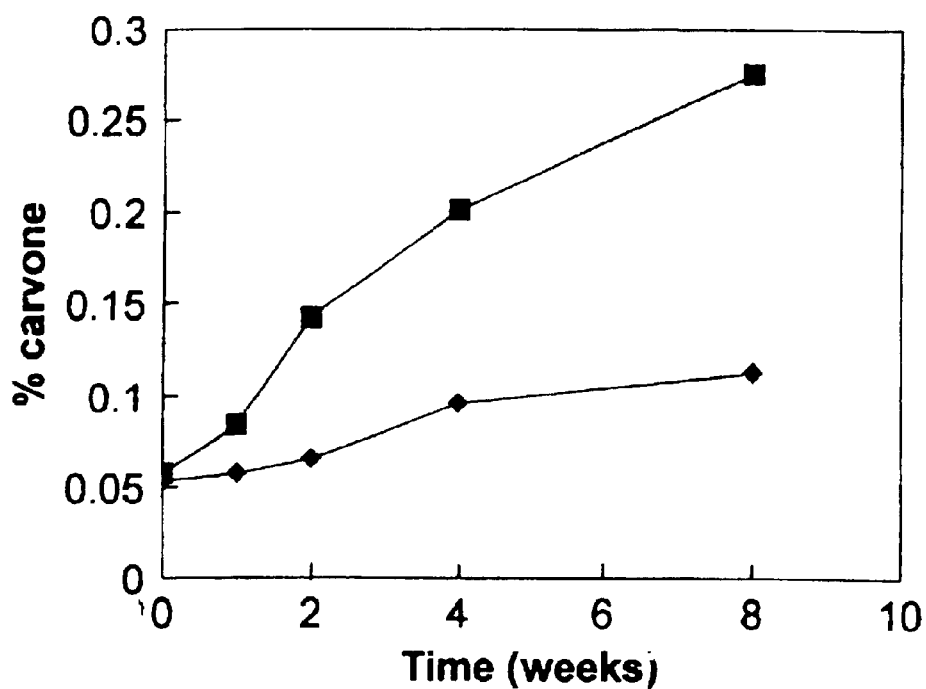

STABLE, SPRAY-DRIED COMPOSITION IN A CARBOHYDRATE SUBSTRATE AND PROCESS FOR OBTAINING SAID COMPOSITION

CROSS-REFERENCED APPLICATIONS

This application is a National phase of International Application PCT/NL00/00840, filed Nov. 17, 2000, which designated the U.S. and that International Application was published under PCT Article 21(2) in English.

The invention relates to a moisture and oxygen stable spray-dried composition comprising at least one active compound like a moisture or oxygen sensitive flavourant, a fragrance or another type of a moisture or oxygen sensitive compound e.g. a pharmaceutical. Further, the invention relates to a process for fixing volatile flavourants, fragrances or other volatile and moisture or oxygen sensitive compounds in an amorphous matrix.

With regard to the field of flavours it is noted that for instance efforts have been made to give the consumer a fresher tasting reconstitutable beverage mix by using certain natural, natural identical or artificial volatile compounds for improving the consumer's taste perception. Unlike liquid systems which usually retain flavourants without adverse stability problems, dry comestible beverage mixes are often lacking in flavour or have off-flavours due to poor storage stability. A fresh tasting, reconstituted beverage would increase the consumer's perception of freshness which is of paramount importance.

Such compounds &a coffee aroma, esters, acetaldehyde, various essential oils and sulphur compounds, augment or enhance the taste perception of convenience foods. Dry comestible mix systems present special problems when one tries to introduce volatile or aromatic flavourants therein. For example, such materials escape through and from the mix, or react so as to degrade or oxidize into compounds which are recognized to be less desirable. Therefore, there has been a long-standing need to fix by encapsulation, and prevent the escape of volatiles within a "powdered-mix" comestible and prevent oxidation thereof. Moreover, the process for fixing a volatile must produce a product which is easily reconstitutable and is capable of holding the fix over prolonged periods and under adverse storage conditions.

A major problem inherent in fixing aromatics in food allowed substrates is the fact that those fixation substrates display idiosyncratic fixation characteristics. The substrate media may be sensitive to moisture, react with the entrained volatile or produce flavour off-notes. Carbohydrates as a class offer a food-acceptable substrate in which volatiles and aromatics have been fixed. However, most water-soluble which volatiles and aromatics have been fixed. However, most water-soluble carbohydrate substrates are hygroscopic and will not reliably hold the fix for long periods. In view of the foregoing, there is a recognized need for an amorphous moisture-stable, water-soluble, food-approved substrate to encapsulate aromatic or volatile flavourants.

Where flavours, such as essential oils, are not protected by an antioxidant, even further problems of off-flavour development are encountered due to oxidation caused by the inability of the carbohydrate matrix to protect the flavour from oxygen.

EP 0,550,067 B1 relates to a method for encapsulating oils such as fragrance and flavouring oils in a water-sensitive cellular solid matrix, comprising drying an aqueous emulsion containing (a) the oil to be encapsulated, (b) a non-crosslinked lipophilically modified starch that undergoes crosslinking under the drying conditions and (c) a polyhydroxy compound that forms with the polysaccharide material a continuous aqueous phase in which the oil is dispersible as a discontinuous phase. The oil (a) which typically contains a conventional antioxidant like butylated hydroxy toluene is typically encapsulated in the dried carbohydrate matrix in an amount from 5 to 80%, preferably at least 65% by weight of the oil and matrix combination. The modified starch (b) is in principle an ungelatinised starch acid ester of a substituted dicarboxylic acid, and the polyhydroxy compound (c) sue polyalcohols like glycerol, mannitol etc., and sugars including mono, di and trisaccharides like glucose, fructose, maltose, sucrose, and raffinose.

U.S. Pat. No. 5,102,682 A relates to a dry flavoured powdered food mix comprising at least 20% crystalline sucrose, at least 10% crystalline fructose, 1–8% crystalline food acid, flavour and anti-caking agent, wherein all components are present in a free, unbound state and wherein the crystalline fructose compound contains less than 10% by weight of particles smaller than 150 $\mu$m. As indicated in said U.S. Pat. No. 5,102,682 the fructose and sucrose content of the food mix can range from 10–60% and 20–80% respectively, and the combined weight of fructose and sucrose will usually be at least 40%, and for soft drink mixes such as fruit-flavoured beverage mixes will typically be at least 90%, usually about 95% or more of the mix.

The flavours suitable for use in the food mix can be spray-dried flavours fixed in a carbohydrate matrix consisting of either maltodextrin or a combination of maltodextrin and a modified starch. According to said U.S. Pat. No. 5,102,682 typical spray-dried flavours contain 30–60% modified food starch and 30–60% maltodextrin and flavourant.

EP 0,426,428 B1 relates to a delivery system for flavours and sweeteners and to a process for its preparation, which system has use in a variety of products including comestibles such as chewing gum, food products etc. More in particular EP 0,426,428 B1 relates to a process for producing a flavour delivery system prepared from a spray-dried emulsion of (a) from 0.1 to 40 wt. % of a flavour oil,
(b) from 0.5 to 30 wt. % of a sweetener and
(c) from 30 to 80 wt. % of a film-forming polymer coating component, all amounts are based on the total weight of the delivery system.

Suitable sweeteners to be encapsulated in the delivery system include natural and artificial high intensity sweeteners selected from amino acid-based sweeteners, dipeptide sweeteners, glycyrrhizin, saccharin and its salts, acesulfame salts, cyclamates, steviosides, talin, sucralose, dihydrochalcone compounds and mixtures thereof. As disclosed therein it is believed that the invention is predicated in part on the discovery that an interaction exists between -flavours and particularly flavour oils and certain intense sweeteners such as aspartame and acesulfame-K when presented in the hydrocollides coatings hereof, such that the sweeteners mask the bitterness of the flavour component. Further, the sequential admixture and emulsification of the ingredients with each other is believed to contribute both to the masking effect exerted on the flavour oil and the improved uniformity and extension of the release and perception of both actives. According to EP 0,426,428 B1 it is further possible to use sweeteners in addition to those already included in the delivery system. Such additional sweeteners, merely used as excipients, may be selected from e.g. sucrose, glucose, dextrose, invert sugar, fructose etc.

U.S. Pat. No. 5,124,162 A is directed to a moisture and oxygen stable spray-dried fixed flavour comprising a flavourant encapsulated in a carbohydrate matrix consisting of 22 to 50%, preferably 22 to 45% mono and disaccharides, wherein at least 50% of the mono and disaccharides is maltose, 25 to 60%, preferably 25 to 50% maltodextrin, and 10 to 40%, preferably 10 to 35% high molecular weight film forming carbohydrate.

With regard to the field of perfumes and perfumed products it is referred to WO 94/19449 indicating the detrimental impact of high humidity conditions on products based on a water sensitive matrix e.g. a starch matrix and a fragrance or a wash-active component encapsulated therein. This type of encapsulates may be added to a number of articles to be perfumed including laundry powder, soap and machine dishwash powder. Apparently the problem encountered in WO 94/19449 is solved by a composition comprising (a) a substance encapsulated within a water-sensitive matrix so as to be releasable upon contact with water or aqueous solutions, mixed with (b) particles of inorganic carrier material carrying a poorly water-soluble oil, such that the composition is stable at high relative humidity. Examples of substances encapsulated in the water-sensitive matrix are a perfume, flavour, a cosmetic ingredient or organometallic complexes e.g. a bleaching agent, bleach activator or bleach catalyst.

Summarizing the prior art it is noted that the most familiar reference is considered U.S. Pat. No. 5,124,162 A. Therein, it is stated that a moisture and oxygen stable spray-dried composition can be obtained if -next to the other two components of the carbohydrate matrix- at least 50% of the mono and disaccharide component is maltose. Further, it is indicated in U.S. Pat. No. 5,124,162 A (column 4, lines 19–23) that certain film forming carbohydrates like gum arabic and waxy starches present "leaky" substrates, which will not retain entrapped volatile flavourants.

Surprisingly, it has now been found that in spite of the above-mentioned prejudice stated in the most familiar reference U.S. Pat. No. 5,124,162 A, a moisture and oxygen stable spray-dried composition could be obtained by using a carbohydrate matrix comprising a rather high amount of 40 to 80 wt. % high molecular weight film forming carbohydrate in combination with 10 to 30 wt. % mono,di and trisaccharides and 10 to 30 wt. % maltodextrin, based on the total weight of the carbohydrate matrix.

Therefore, the invention relates to a moisture and oxygen stable spray-dried composition comprising at least one active compound encapsulated in a carbohydrate matrix which matrix is characterized by 40 to 80 wt. % high molecular weight film forming carbohydrate;

10 to 30 wt. % mono, di and trisaccharides; and 10 to 30 wt. % maltodextrin based on the total weight of the carbohydrate matrix.

In view of the above discussed U.S. Pat. No. 5,124,162 A, it is stated that the maltose percentage of the saccharide component in the spray-dried composition according to the invention may be less than 50% and even nihil in case for instance sucrose is used as the only saccharide component therein.

More in particular the carbohydrate matrix includes from 45 to 70 wt. %, preferably from 50 to 60 wt. % high molecular weight film forming carbohydrate. Suitable film forming carbohydrates are film forming gums, pectins, alginates, mucilages and mixtures thereof. Preferably the film forming carbohydrates are selected from gum arabic, gum acacia, tragacanth, karaya, ghatti, agar, alginates, carrageenans, fucellan, psyllium and mixtures thereof or from gelatin, dextran, xanthan, curdlan, cellulose, methylcellulose, ethylcellulose, hydroxyethylcellulose, hydroxypropyl cellulose, hydroxypropyl methylcellulose, carboxymethyl cellulose, low methoxy pectin, propylene glycol alginate and mixtures thereof.

Most preferably the film forming agents are film forming gums, hydrocolloids and lipophilically modified starches. Examples of gums are gum arabic and gum acacia. Examples of suitably chemically modified starches are Capsul® and N-Lok (National Starch). Of course, also mixtures of film forming carbohydrates can be used in the spray-dried compositions according to the invention.

Another component of the carbohydrate matrix according to the invention are the mono, di and trisaccharides, which are used in an amount of 10 to 30 wt. %, preferably 15–25 wt. %, based on the total weight of the carbohydrate matrix. Illustrative examples of mono, di and trisaccharides are glucose, fructose, maltose, sucrose, raffinose and materials, having a high content of such sugars like fruit juice solids. Preferably, at least 50 wt. % of the mono, di and trisaccharide material is a disaccharide as a high amount of monosaccharide may result in a somewhat sticky product whereas a high amount of trisaccharide may lead to a product more prone to oxidation. In a preferred embodiment according to the invention the mono, di and trisaccharide material is sucrose.

For instance, a moisture and oxygen stable spray-dried composition can comprise at least one active compound encapsulated in a carbohydrate matrix, which matrix can be characterized by 40 to 80 wt. % high molecular weight film forming carbohydrate; 10 to 30 wt. % mono, di and trisaccharides; and 10 to 30 wt. % maltodextrin, with the wt. % being based on the total weight of the carbohydrate matrix. In one of the embodiments, sucrose can comprise 100 wt. % of the mono, di and trisaccharide material.

The carbohydrate matrix according to the invention further includes 10 to 30 wt. %, preferably 10 to 25 wt. % maltodextrin. The maltodextrin will preferably have a dextrose equivalent (DE) in the range of 1 to 25, most preferably in the range of 10 to 20. A variety of maltodextrins meeting the above requirements are readily available commercially, including maltodextrins from e.g. tapioca, maize and potato.

The carbohydrate matrix may be softened by the incorporation of up to 5 wt. % of an edible polyol such as glycerol, preferably 1 to 3 wt. %, based on the carbohydrate matrix. Also other components like anti-foam agents in an amount of up to 0.2‰ may be added.

The active compound to be encapsulated in the carbohydrate matrix can be selected from the group consisting of flavourants, fragrances, pharmaceuticals and wash-active components.

Flavourants are well-known in the art and are mentioned, e.g., in S. Arctander, Perfume and Flavor Materials of Natural Origin (Elisabeth, N.J., USA; 1996), in T. E. Furia et al, CRC Fenaroli's Handbook of Flavor Ingredients, 2nd Ed. (Cleveland, CRC Press Inc., 1975), and in H. B. Heath, Source Book of Flavors (The Avi Publishing Company Inc., Westport, Conn., 1981).

Fragrances and mixtures thereof which can be used for the preparation of perfumed articles are e.g. naturally occurring products such as essential oils, absolutes resinoids, resins, concretes etc., natural, nature identical and artificial fragrances, such as hydrocarbons, alcohols, aldehydes, ketones, ethers, acids, esters, acetals, ketals, nitrites etc., covering saturated and unsaturated compounds, aliphatic, carbocyclic and heterocyclic compounds, for instance as disclosed in S.Arctander (loc.cit.).

Examples of fragrances which may be used within the scope of the invention are: geraniol, geranyl acetate, linalool, linalyl acetate, tetrahydrolinalool, citronellol, citronellyl acetate, dihydro myrcenol, dihydro myrcenyl acetate, tetrahydro myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert.butylcyclohexyl acetate, isononyl acetate, vetiveryl acetate, vetiverol, α-hexyl-cinnamaldehyde, 2-methyl-3-(p-tert.butyiphenyl)-propanal, 2-methyl-3-(p-isopropylphenyl)-propanal, 3-(p-tert.butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentanone, n-decanal, n-dodecanal, dec-9-en-1-ol, phenoxy-ethyl isobyutyrate, phenylacetaldehyde dimethylacetal, phenylacetaldehyde diethylacetal, geranyl nitrile, citronellyl nitrile, cedryl acetate, 3-isocamphyl cyclohexanol, cedrylmethyl ether, isolongifolanone, aubepine nitrile, aubepine, heliotropine, coumarin, eugenol, vanillin, diphenyl oxide, hydroxy citronellal, ionones, methyl ionones, isomethyl ionones, irones, cis-3-hexenol and esters thereof, indan musk fragrances, tetralin musk fragrances, isochroman musk frangrances, macrocyclic ketones, macrolactone musk fragrances, ethylene brassylate, aromatic nutri-musk frangrances.

The fragrance comprising spray-dried products according to the invention may be used successfully in perfumed articles. Examples of such perfumed articles are: soap, bath products, washing agents, dish washing and cleaning agents, pommanders, candles, cosmetics such as creams, ointments, body deodorant sticks and antiperspirant sticks.

Also pharmaceuticals and wash-active components which are prone to humidity or oxygen can be used as active compound to be encapsulated in the carbohydrate matrix according to the invention.

A major application of the invention is related to the field of flavours. In this respect it is noted that the final spray-dried product according to the invention is capable of protecting and retaining 5 to 40 wt. % or even more, preferably 20 to 30 wt. % flavourant as active compound, depending on the type of flavourant and based on the total weight of the flavour. Examples of flavourants, in particular aromatic or volatile flavourants, to be encapsulated in the carbohydrate matrix according to the invention are for instance essential oils, like citrus oil, e.g. lemon oil, orange oil, grapefruit oil and other volatile flavourants, like bakery and savoury flavourants. Also other types of active compounds as indicated above can be encapsulated in the carbohydrate matrix according to the invention in an amount of 5–40 wt. % or more, preferably 20–30 wt. %, based on the total weight of the composition.

A further aspect of the invention is embodied by a process for producing the moisture and oxygen stable composition, comprising the steps of
  a) forming an aqueous carbohydrate solution containing, a carbohydrate mixture consisting of 40 to 80 wt. % high molecular weight film forming carbohydrate(s), 10 to 30 wt. % mono, di and trisaccharide(s), and 10 to 30 wt. % maltodextrin(s),
  b) incorporating at least one active compound defined above into the solution of step (a), and
  c) spray-drying the aqueous solution of step (b) using an outlet temperature of 100° C. or less to obtain a stable product encapsulated therein the active compound.

In general, the procedure of spray-drying involves the following. At first a solution of the product one wishes to make is prepared. The term solution is understood to mean mixtures of solutes and solvents encompassing such mixtures as emulsions or dispersions. The solution is fed into an atomizer which creates a fine mist, composed of regular-sized droplets. The misted solution is introduced, usually through the top of a drying tower or chamber into the spraydryer. Heated air is fed into the chamber so that as the droplets fall from the top of the chamber evaporation and drying of the aqueous liquid phase respectfully occurs. The product is collected from an outlet port. Examples of spray-drying apparatus are the Anhydro Dryers (manufactured by Anhydro Corp. of Attleboro Falls, Mass. U.S.A.) or the Niro Dryer (manufactured by Niro Atomizer Ltd, Copenhagen, Denmark).

More in particular the combination of carbohydrate materials is dissolved in water to form an aqueous solution with the temperature being maintained at around 10° C. to 90° C. In the case of a highly volatile substance the solution is allowed to cool to about the boiling point of the substance or below. The active compound, for instance a volatile or aromatic flavourant is then added to the solution, the solution being preferably maintained at from 10° C. to 50° C. The solution is then spray-dried in an atmospheric spraydryer wherein the inlet temperature is typically about 140° C. to 210° C. and the outlet temperature typically 70° C. to 100° C. The resultant moisture-stable product has an excellent retention of volatiles over time and a prolonged shelf life without unacceptable oxidation. No antioxidant is added or made part of the final product.

Figure 2:
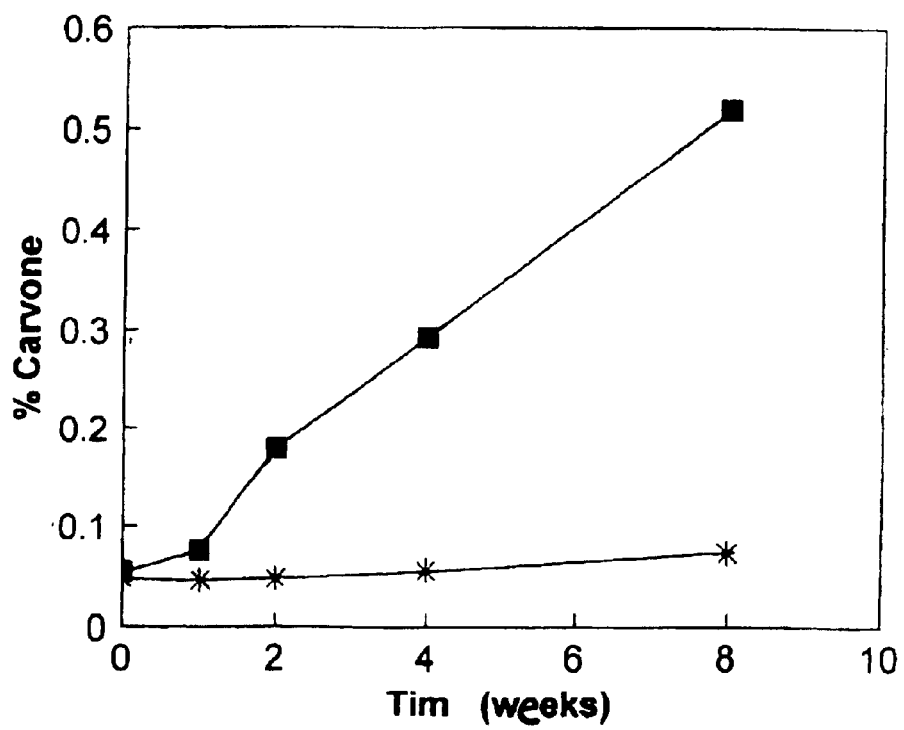

The invention is elucidated by means of the following examples and the storage properties of the spray-dried products are illustrated by means of the FIGS. 1 and 2.

Figure 3:
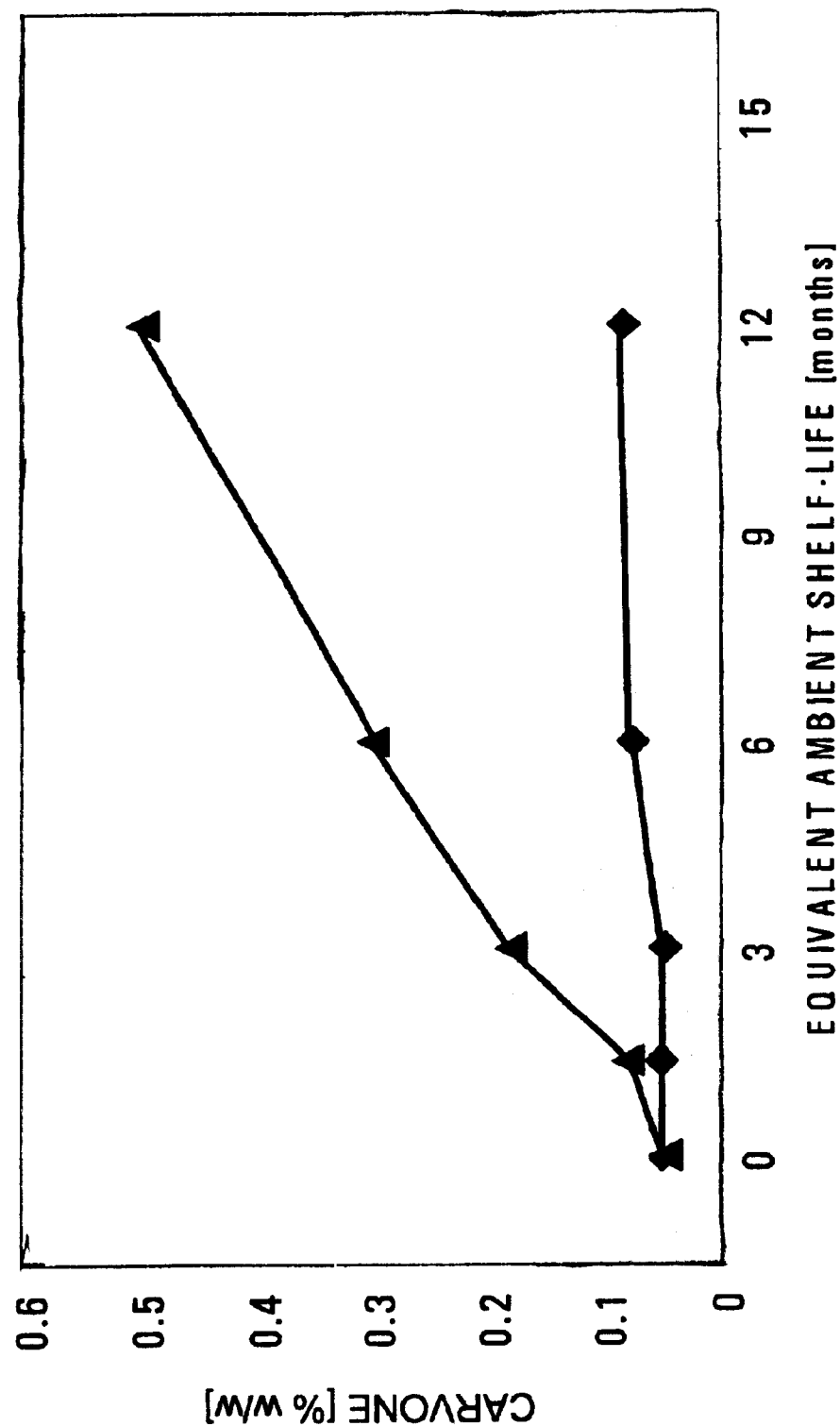

FIG. 1 illustrates the accelerated shelf life test of
  a product according to the prior art based on 25 wt. % orange flavourant (QL 06830 marketed by Quest International, the Netherlands) and 75 wt. % of a carbohydrate matrix consisting of 50 wt. % Capsul® and 50 wt. % maltodextrin (DE 20), and
  a product according to the invention based on 25 wt. % orange flavourant (QL 06830) and 75 wt. % of a carbohydrate matrix consisting of 50 wt. % Capsul®, 23 wt. % maltodextrin (DE 20), 25 wt. % sucrose and 2 wt. % glycerol.
    More in particular the X-axis represents the time in weeks, and the Y-axis represents the amount of carvone in wt. %, formed from the spray-dried products due to oxidation of the limonene component of the used orange flavourant during the accelerated shelf life test at 40° C. and at a relative humidity (RH) of 30%.
FIG. 2 illustrates the accelerated shelf life test of
  the product according to the prior art shown in FIG. 1, and
  a product according to the invention based on 25 wt. % orange flavourant (QL 06830) and 75 wt. %. of a carbohydrate matrix consisting of 60 wt. % gum acacia, 20 wt. % maltodextrin (DE 10) and 20 wt. % sucrose.
    More in particular the X-axis represents the time in weeks, and the Y-axis represents the amount of carvone in wt. %, formed from the spray-dried products due to oxidation of the limonene component of the used orange flavourant during the accelerated shelf life test at 40° C. and at a relative humidity (RH) of 50%.
FIG. 3 illustrates the accelerated shelf life test of
  the product according to the prior art shown in FIG. 1, and a product according to the invention based on 25 wt. % orange flavourant (QL 06830) and 75 wt. % of a carbohydrate matrix consisting of 50 wt. % Capsul®, 30 wt. % maltodextrin (DE 20) and 20 wt. % glucose.

More in particular the X-axis represents the equivalent ambient shelf-life in months, and the Y-axis represents the amount of carvone in wt. %, formed from the spray-dried products due to oxidation of the limonene component of the used orange flavourant during the accelerated shelf life test at 40° C. and at a relative humidity (RH) of 30%.

Figure 4:
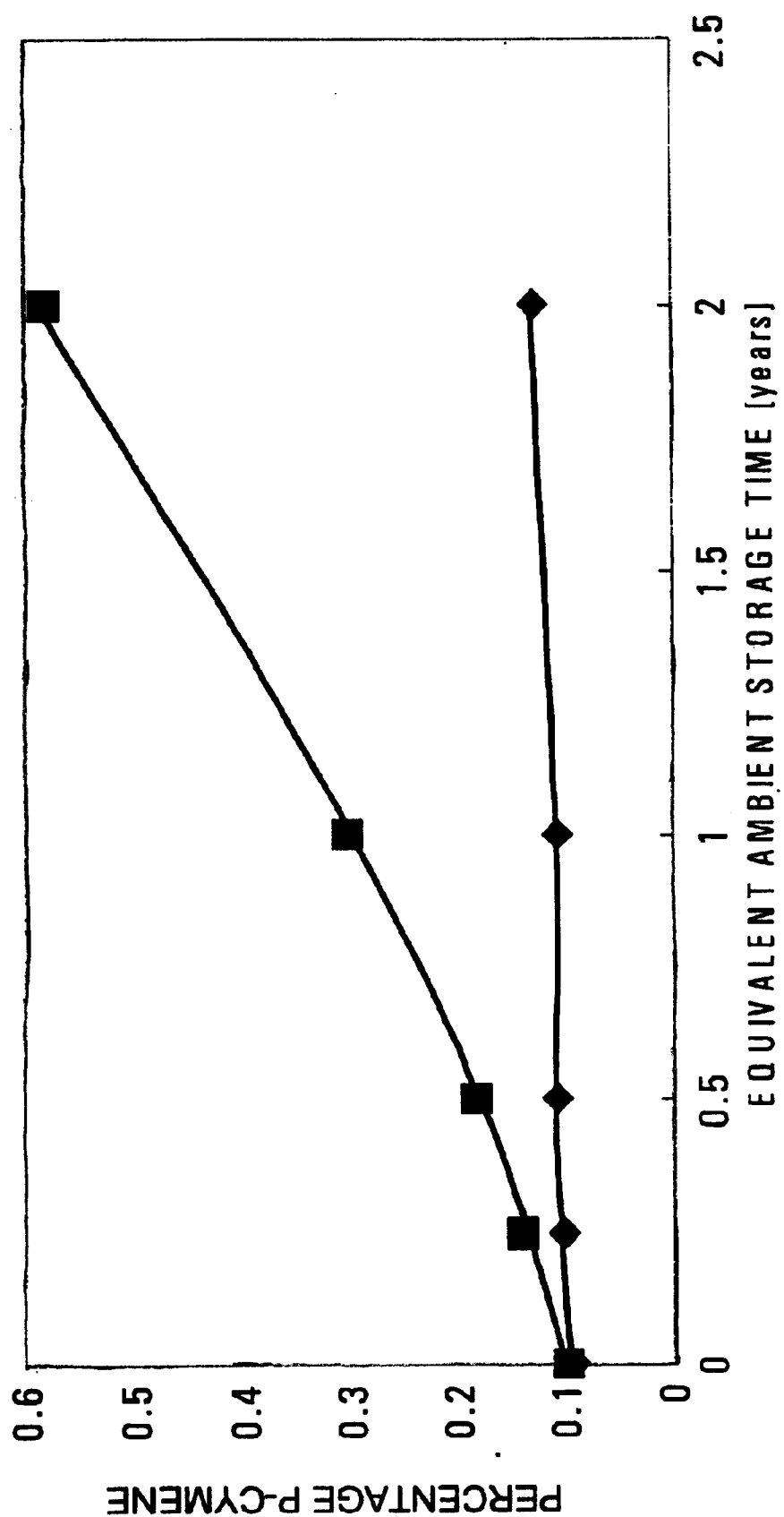

FIG. 4 illustrates the accelerated shelf-life test of the product according to the prior art shown in FIG. 1, and a product according to the invention based on 25 wt. % mandarin flavourant (DF 39467) and 75 wt. % of a carbohydrate matrix consisting of 60 wt. % gum acacia, 20 wt. % maltodextrin (DE 10), 9 wt. % mandarin juice solids and 11 wt. % sucrose (total sugar content: 19 wt. %).

More in particular the X-axis represents the equivalent ambient shelf-life in months, and the Y-axis represents the amount of p-cymene in wt. %, formed from the spray-dried products due to oxidation of the terpene compounds in the used mandarin flavourant during the accelerated shelf life test at 40° C. and at a relative humidity (RH) of 50%.

EXAMPLE 1

The following two formulations were prepared by dissolving or dispersing the components indicated below
  (a) 500 g of a carbohydrate matrix comprising 50 wt. % (250 g) Capsul® and 50 wt. % (250 g) maltodextrin (DE 20) being a carbohydrate matrix used for marketed products; and
  (b) 500 g of a carbohydrate matrix consisting of 50 wt. % (250 g) Capsul®, 23 wt. % (115 g) maltodextrin (DE 20), 25 wt. % (125 g) sucrose and 2 wt. % (10 g) glycerol being a carbohydrate matrix according to the invention
under stirring in 600 g warm water of 80° C. for 30 minutes. Then the mixture was cooled to 20° C. An orange flavourant (QL 06830) without any antioxidant preservative was added in an amount of 25 wt. % on total dry solids (166 g) under stirring and the prepared feed was homogenised using a Ultra Turrax T50 at 10,000 rpm for about 3 minutes. The homogenised feed was spray dried in a NIRO MOBIL MINOR SPRAY DRYER using a rotary wheel atomiser at 20,000 rpm. Inlet air temperature was kept at 190° C., resulting in an outlet temperature in the range of 90° C.

As apparent from FIG. 1, the product according to the invention had an excellent stability and a desired long storage life compared to the prior art product. More in particular the storage time of 8 weeks in the accelerated shelf life test at 40° C. and a RH of 30% corresponds to a storage time of about one year at room temperature (20° C.) and a RH of 30%.

EXAMPLE 2

The following two formulations were prepared by dissolving or dispersing the components indicated below
  (a) 500 g of a carbohydrate matrix consisting of 50 wt. % (250 g) Capsul® and 50 wt. % (250 g) maltodextrin (DE 20) being a carbohydrate matrix used for marketed products; and
  (b) 316 g of a carbohydrate matrix consisting of 60 wt. % (190 g) gum acacia, 20 wt. % (63 g) maltodextrin (DE 10) and 20 wt. % (63 g) sucrose being a carbohydrate matrix according to the invention
under stirring in 600 g warm water of 60° C. for 30 minutes. Then the mixture was cooled to 20° C. An orange flavourant (QL 06830) without any antioxidant preservative was added in an amount of 25 wt. % on total dry solids (166 g for formulation (a) and 105 g for formulation (b)) under stirring and the prepared feed was homogenised using a Ultra Turrax T50 at 10,000 rpm,for about 3 minutes. The homogenised feed was spray-dried in a NIRO MOBIL MINOR SPRAY DRYER using a rotary wheel atomiser at 20,000 rpm. Inlet air temperature was kept at 190° C., resulting in an outlet temperature in the range of 90° C.

As apparent from FIG. 2, the product according to the invention had an excellent stability and a desired long storage life compared to the prior art product. More in particular the storage time of 8 weeks in the accelerated shelf life test at 40° C. and a RH of 50% corresponds to a storage time of about one year at room temperature (20° C.) and a RH of 50%.

EXAMPLE 3

The following two formulations were prepared by dissolving or dispersing the components indicated below
  (a) 500 g of a carbohydrate matrix comprising 50 wt. % (250 g) Capsul® and 50 wt. % (250 g) maltodextrin (DE 20) being a carbohydrate matrix used for marketed products; and
  (b) 500 g of a carbohydrate matrix consisting of 50 wt. % (250 g) Capsul®, 30 wt. % (150 g) maltodextrin (DE 20), and 20 wt. % (100 g) glucose being a carbohydrate matrix according to the invention
under stirring in 600 g warm water of 80° C. for 30 minutes. Then the mixture was cooled to 20° C. An orange flavourant (QL 06830) without any antioxidant preservative was added in an amount of 25 wt. % on total dry solids (166 g) under stirring and the prepared feed was homogenised using a Ultra Turrax T50 at 10,000 rpm for about 3 minutes. The homogenised feed was spray-dried in a NIRO MOBIL MINOR SPRAY DRYER using a rotary wheel atomiser at 20,000 rpm. Inlet air temperature was kept at 190° C., resulting in an outlet temperature in the range of 90° C.

As apparent from FIG. 3, the product according to the invention had an excellent stability and a desired long storage life compared to the prior art product. More in particular the storage time of 8 weeks in the accelerated shelf life test at 40° C. and a RH of 30% corresponds to an ambient shelf-life of about one year at room temperature (20° C.) and a RH of 30%.

EXAMPLE 4

The following two formulations were prepared by dissolving or dispersing the components indicated below
  (a) 500 g of a carbohydrate matrix comprising 50 wt. % (250 g) Capsul® and 50 wt. % (250 g) maltodextrin (DE 20) being a carbohydrate matrix used for marketed products; and
  (b) 316 g of a carbohydrate matrix consisting of 60 wt. % (190 g) gum acacia, 20 wt. % (63 g) maltodextrin (DE 10), 9 wt. % (28.5 g) mandarin juice solids (90–95% of juice solids (D. S.) is a sugar mixture consisting of glucose and fructose) and 11 wt. % (34.5 g) sucrose being a carbohydrate matrix according to the invention (the resulting sugar content originating from the sum of the sucrose and the sugars present in the fruit juice concentrate is 19 wt. % of sugars)

under stirring in 600 g warm water of 80° C. for 30 minutes. Then the mixture was cooled to 20° C. A mandarin flavourant (DF 39467) without any antioxidant preservative was added in an amount of 25 wt. % on total dry solids (166 g) under stirring and the prepared feed was homogenised using a Ultra Turrax T50 at 10,000 rpm for about 3 minutes. The homogenised feed was spray-dried in a NIRO MOBIL MINOR SPRAY DRYER using a rotary wheel atomiser at 20,000 rpm. Inlet air temperature was kept at 190° C., resulting in an outlet temperature in the range of 90° C.

As apparent from FIG. 4, the product according to the invention had an excellent stability and a desired long storage life compared to the prior art product. More in particular the storage time of 8 weeks in the accelerated shelf life test at 40° C. and a RH of 30% corresponds to an ambient shelf-life of about one year at room temperature (20° C.) and a RH of 30%.

What is claimed is:

1. A moisture and oxygen stable spray-dried composition comprising at least one active compound encapsulated in a carbohydrate matrix, which matrix is characterised by 45 to 75 wt. % high molecular weight film forming carbohydrate;

10 to 30 wt. % mono, di and trisaccharides; and 10 to 30 wt. % maltodextrin, wherein said wt. % are based on the total weight of the carbohydrate matrix.

2. The spray-dried composition according to claim 1, wherein said film forming carbohydrate is present in an amount of 50–60 wt. % based on the total weight of the carbohydrate matrix.

3. The spray-dried composition according to claim 1 or 2, said film forming carbohydrate is selected from the group consisting of gum arabic, gum acacia, lipophilically modified starches and mixtures thereof.

4. The spray-dried composition according to any one of claim 1 or 2, wherein said mono, di and trisaccharides are present in an amount of 15–25 wt. % based on the total weight of the carbohydrate matrix.

5. The spray-dried composition according to any one of claim 1 or 2, wherein at least 50 wt. % of the mono, di and trisaccharide material is a disaccharide.

6. The spray-dried composition according to claim claim 1 or 2, wherein said carbohydrate matrix includes, as a disaccharide, is sucrose.

7. The spray-dried composition according to claim 5, wherein 100 wt. % of the mono, di and trisaccharide material is sucrose.

8. The spray-dried composition according to any one of claim 1 or 2, wherein said maltodextrin has a dextrose equivalent (DE) in the range of 1 to 25.

9. The spray-dried composition according to any one of claim 1 or 2, wherein said active component encapsulated in the carbohydrate matrix is selected from the group consisting of flavorants, fragrances, pharmaceuticals and wash-active components.

10. The spray-dried composition according to any one of claim 1 or 2, wherein said encapsulated active compound is at least one flavorant selected from the group consisting of essential oils, bakery flavorants and savoury flavorants.

11. The spray-dried composition according to any one of claims claim 1 or 2, wherein said encapsulated active compound is present in an amount of 5–40 wt. % based on the total weight of the composition.

12. A process for producing a moisture and oxygen stable composition comprising the steps of:

(a) forming an aqueous carbohydrate solution containing a carbohydrate mixture consisting of 45 to 75% high molecular weight film forming carbohydrate(s), 10 to 30 wt. % mono, diu and trisaccharide(s), and 10 to 30 wt. % maltodextrin(s);

(b) incorporating at leat one active compound into the solution of step (a); and (c) spray-dried the aqueous solution of step (b) using an outlet air temperature of 100° C. or less, to obtain a stable product having encapsulated therein the active compound.

13. The process according to claim 12, wherein said active compound is selected from the group consisting of flavorants, fragrances, pharmaceuticals and wash-active compounds.

14. A product comprising the spray-dried composition prepared by the process according to claim 12 or 13.

15. The spray-dried composition according to claim 3, wherein said mono, di and trisaccharides are present in a amount of 15–25 wt. % based on the total weight of the carbohydrate matrix.

16. The spray-dried composition according to claim 15, wherein at least 50 wt. % of the mono, di and trisaccharide material is a disaccharide.

17. The spray-dried composition according to claim 15, wherein said disaccharide is sucrose.

18. The spray-dried composition according to claim 15, wherein 100 wt. % of the mono, di and trisaccharide material is sucrose.

19. The spray-dried composition according to claim 8, wherein said maltodextrin has a dextrose equivalent (DE) in the range of 10 to 20.

20. The spray-dried composition according to claim 3, wherein said active component encapsulated in the carbohydrate matrix is selected from the group consisting of flovorants, fragrances, pharmaceuticals and wash-active components.

21. The spray-dried composition according to claim 10, wherein said essential oil is a citrus oil.

22. The spray-dried composition according to claim 21, wherein said citrus oil is selected from the group consisting of lemon oil, orange oil and grapefruit oil.

23. The spray-dried composition according to claim 3, wherein said encapsulated active compound is present in am amount of 20–30 wt. %, base on the total of the composition.

24. The spray-dried composition according to claim 5, wherein said disaccharide is sucrose.

25. The spray-dried composition according to claim 1, wherein said mono, di and trisaccharides include less than 50 wt. % of maltose.

* * * * *